(12) United States Patent
Takahashi (10) Patent No.: US 7,232,410 B2
(45) Date of Patent: Jun. 19, 2007

(54) ADJUSTING METHOD FOR ENDOSCOPE SYSTEMS

(75) Inventor: Tomoya Takahashi, Akiruno (JP)

(73) Assignee: Olympus Corporation, Tokyo (JP)

( * ) Notice: Subject to any disclaimer, the term of this patent is extended or adjusted under 35 U.S.C. 154(b) by 334 days.

(21) Appl. No.: 10/726,937

(22) Filed: Dec. 3, 2003

(65) Prior Publication Data

US 2004/0122291 A1 Jun. 24, 2004

Related U.S. Application Data

(63) Continuation of application No. PCT/JP02/11091, filed on Oct. 25, 2002.

(30) Foreign Application Priority Data

Oct. 30, 2001 (JP) .............................. 2001-333126

(51) Int. Cl.
*A61B 1/06* (2006.01)

(52) U.S. Cl. ..................... 600/180; 600/181; 348/69; 348/70

(58) Field of Classification Search ................ 600/178, 600/180, 181; 348/68–70, 74; 362/574
See application file for complete search history.

(56) References Cited

U.S. PATENT DOCUMENTS

| | | | | |
|---|---|---|---|---|
| 4,509,508 | A | * | 4/1985 | Tsukaya ..................... 600/118 |
| 4,713,683 | A | * | 12/1987 | Fujimori et al. ............ 348/269 |
| 4,800,424 | A | | 1/1989 | Noguchi |
| 4,866,526 | A | * | 9/1989 | Ams et al. ..................... 348/69 |
| 5,187,572 | A | * | 2/1993 | Nakamura et al. ............ 348/68 |
| 5,408,263 | A | * | 4/1995 | Kikuchi et al. ............... 348/68 |
| 5,589,879 | A | * | 12/1996 | Saito et al. .............. 348/223.1 |
| 5,868,666 | A | | 2/1999 | Okada et al. |
| 6,080,104 | A | * | 6/2000 | Ozawa et al. ............... 600/180 |
| 6,353,709 | B1 | | 3/2002 | Miyazaki et al. |
| 6,700,619 | B1 | * | 3/2004 | Hamamura ................. 348/370 |
| 6,822,677 | B1 | * | 11/2004 | Takahashi ................ 348/223.1 |
| 6,876,157 | B2 | * | 4/2005 | Henry ........................ 315/219 |
| 6,980,227 | B2 | * | 12/2005 | Iida et al. ..................... 348/69 |
| 2002/0196335 | A1 | * | 12/2002 | Ozawa ........................ 348/70 |
| 2004/0215060 | A1 | * | 10/2004 | Ueno et al. ................. 600/160 |

FOREIGN PATENT DOCUMENTS

| | | |
|---|---|---|
| DE | 195 29 164 A1 | 2/1996 |
| JP | 61-61586 | 3/1986 |
| JP | 61-103385 | 5/1986 |

(Continued)

*Primary Examiner*—John P. Leubecker
(74) *Attorney, Agent, or Firm*—Scully, Scott, Murphy & Presser, P.C.

(57) ABSTRACT

An adjusting method for endoscope systems comprises a first adjusting step, a second light adjusting step and a storing step. The first adjusting step compares video signals, which are produced from illumination light rays that are reflected from an object and whose wavelengths fall within first, second, and third ranges, with one another, and regulates a lamp current that flows into a light source lamp. The second light adjusting step adjusts a diaphragm that controls an amount of light which is emitted from the light source lamp and which is irradiated to the object. The storing step stores the lamp current regulated at the first adjusting step and a light limiting level adjusted at the second adjusting step.

9 Claims, 5 Drawing Sheets

FOREIGN PATENT DOCUMENTS

| | | |
|---|---|---|
| JP | 63-155984 | 6/1988 |
| JP | 4-245887 | 9/1992 |
| JP | 7-184109 | 7/1995 |
| JP | 10-262922 | 10/1998 |
| JP | 11-076158 | 3/1999 |
| JP | 2000-267166 | 9/2000 |

* cited by examiner

ADJUSTING METHOD FOR ENDOSCOPE SYSTEMS

CROSS REFERENCE TO RELATED APPLICATION

This application is a continuation application of PCT/JP02/11091 filed on Oct. 25, 2002 the disclosure of which is incorporated herein by its reference.

TECHNICAL FIELD

The present invention relates to an adjusting method for endoscope systems according to which white balance adjustment and light level adjustment are performed on illumination light irradiated from a light source by utilizing a field-sequential image production method.

BACKGROUND ART

Electronic endoscope systems adopt either a field-sequential technique or a simultaneous technique. According to the field-sequential technique, red (R), green (G), and blue (B) illumination light rays are irradiated to an object. The red, green, and blue illumination light rays reflected from the object are converged on a solid-state imaging device, red, green, and blue video signals produced by the solid-state imaging device are synthesized to produce a color video signal. According to the simultaneous technique, white light reflected from an object is split into red, green, and blue object light rays using a color filter. Solid-state imaging devices associated with red, green, and blue produce video signals from the red, green, and blue object light rays, and the object video signals are synthesized to produce a color video signal.

Many endoscopes adopt the field-sequential technique because an insertion member to be inserted into a body cavity must be thin and a produced video signal must offer a high resolution.

An electronic endoscope system adopting the field-sequential technique is disclosed in, for example, Japanese Patent No. 306123. Illumination light irradiated from a light source lamp is propagated to a light guide by way of a rotary filter and a condenser lens. The illumination light guided by the light guide is irradiated to an object, and light reflected from the object is converged on a solid-state imaging device.

The rotary filter is driven to rotate at a predetermined rps using a motor. Light is passed through red, green, and blue transmission filters that cover three fan-shaped openings formed on the perimeter of the rotary filter. Consequently, red, green, and blue illumination light rays are irradiated to an object.

The red, green, and blue light rays produced by the rotary filter and reflected from the object are converged on the solid-state imaging device. Red, green, and blue video signals produced by the solid-state imaging device are synthesized to produce a color video signal.

A photosensor is provided on the rotary filter at the perimeter thereof to detect an open period of the openings. The photosensor detects a pulse signal that indicates the open period of the openings. Using the pulse signal, a pulse current for lighting the light source lamp is produced.

In other words, during the open period of the openings covered with the red, green, and blue transmission filters included in the rotary filter is unblocked, the pulse current is superposed on a predetermined constant current which lights the light source lamp. The resultant current is then supplied to the light source lamp.

When the light source lamp is lit using the pulse current, a white balance can be readily adjusted within a light source device by controlling the duty cycle or value of the pulse current.

In a conventional electronic endoscope, illumination light irradiated from a light source lamp is converted into red, green, and blue illumination light rays using red, green, and blue transmission filters included in a rotary filter. The red, green, and blue illumination light rays are propagated over a light guide, and successively irradiated to an object. Red, green, and blue object light rays reflected from the object are converged on a solid-state imaging device, and photoelectrically converted into red, green, and blue object video signals.

The red, green, and blue object video signals are synthesized to produce a television video signal. When the television video signal is produced by synthesizing the object video signals, white balance adjustment is needed in order to synthesize the red, green, and blue object video signals at a predetermined ratio.

The white balance adjustment falls into a method for adjusting a lighting current for lighting a light source lamp with each red, green, and blue transmission filter provided at the openings of the rotary filter, and a method for electrically synthesizing the red, green, and blue object video signals produced by the solid-state imaging device.

Aside from the white balance adjustment, driving of a diaphragm that optimizes an amount of illumination light which is emitted from the light source lamp and irradiated to an object by way of the rotary filter and light guide must be controlled.

The regulation of a lighting current for lighting the light source lamp and control of driving of the diaphragm that adjusts an amount of light irradiated to an object, which are required for the white balance adjustment, are achieved by a skilled worker, who uses a predetermined adjustment jig, in the course of manufacturing the electronic endoscope system. Moreover, when the light source lamp included in the electronic endoscope system is replaced with a new one because of termination of the service life thereof, or when the light source lamp is repaired, the white balance adjustment and the adjustment of the diaphragm for regulation of the brightness level of a view image must be performed again using the adjustment jig.

As mentioned above, especially when the light source lamp is replaced with a new one or repaired, the white balance adjustment and the adjustment of the brightness level of a view image must be performed again. At this time, the adjustment jig is needed as a repairing instrument. Moreover, a worker skilled in the white balance adjustment or the adjustment of the brightness in a view image must perform the adjustment by taking much time.

Accordingly, an object of the present invention is to provide an adjusting method for endoscope systems that permits quick and reliable white balance adjustment and light level adjustment for illumination light without the necessity of an adjustment jig.

DISCLOSURE OF INVENTION

An adjusting method for endoscope systems in accordance with the present invention comprises:
a first adjusting step of comparing video signals, which are produced from illumination light rays that are reflected from an object and whose wavelengths fall within first, second, and third ranges, with one another so as to regulate a lamp current to be supplied to a light source lamp;

a second light adjusting step of adjusting a diaphragm that controls an amount of light which is emitted from the light source lamp and irradiated to the object;

a storing step of storing the lamp current regulated at the first adjusting step and a light limitation level adjusted at the second adjusting step.

BEST MODE FOR CARRYING OUT THE INVENTION

Referring to FIG. 1 to FIG. 4, a first embodiment of the present invention is described below in detail.

Figure 1:
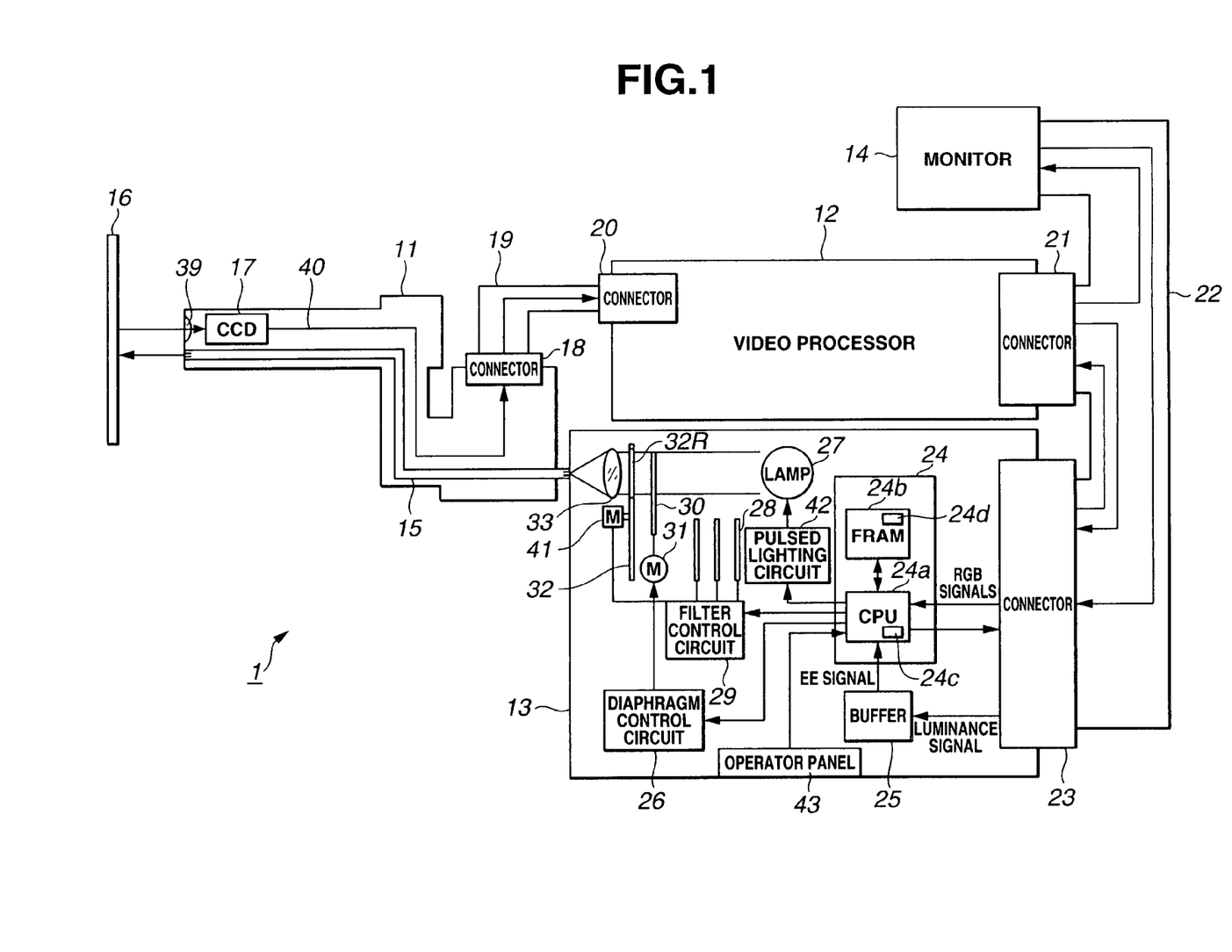
FIG. 1 is a block diagram showing an endoscope system in which a first embodiment of the present invention is implemented.

As shown in FIG. 1, an endoscope system 1 in which the first embodiment of the present invention is implemented comprises an endoscope (hereinafter, referred to as scope) 11, a video processor 12, a light source device 13, and a monitor 14.

The endoscope 11 includes an insertion member that is inserted into a body cavity and an operating member proximal to the insertion member. A light guide 15 over which illumination light emanating from the light source device 13 is propagated lies through the operating member and reaches the distal end of the insertion member. The illumination light is irradiated to an object 16 from the distal end of the light guide 15.

An objective lens 39 that forms an object image under light reflected from the object 16, and a charge-coupled device (hereinafter, referred to as CCD) 17 serving as a solid-state imaging device and being located on the image plane of the objective are incorporated in the distal portion of the insertion member.

The CCD 17 photoelectrically coverts the formed object image so as to produce an object video signal (or image signal). An image signal line 40 over which a driving control signal and the object video signal resulting from photoelectric conversion are inputted is coupled to the CCD 17. The image signal line 40 lies through the insertion member and operating member alike, and is connected to a connector 18 formed at the proximal end of the operating member.

The light guide 15 comprises a light guide fiber bundle. A light guide connector fixed to the end of the light guide 15 is connected to the light source device 13 over a light guide cable.

The connector 18 formed in the endoscope 11 is connected to a connector 20 formed in the video processor 12 over an electric cable (EL cable) 19 incorporated in an electric signal line that is connected to the image signal line 40.

The video processor 12 captures a driving signal which drives the CCD 17, and an object video signal produced by the CCD 17, and processes the captured object video signal so as to produce a television video signal. Based on the television video signal, a display signal according to which an object picture is displayed on the monitor 14, a luminance signal for controlling the light source device 13, and a sync signal are produced.

A connector 21 is formed in the video processor 12. Red, green, and blue signals for displaying an object image on the monitor 14 are transferred through the connector 21 over a communication cable 22. Moreover, the luminance signal and sync signal are transferred to the light source device 13 through the connector 21. Incidentally, the luminance signal is used to adjust the diaphragm 31 as described later.

The light source device 13 has a connector 23 into which the communication cable 22 is plugged. The light source device 13 includes a controller 24, a buffer 25, a diaphragm control circuit 26, a light source lamp 27, a specific filter 28, a filter control circuit 29, a diaphragm 30, a diaphragm motor 31, a RGB filter 32, a condenser lens 33, and a pulse lighting circuit 42.

The controller 24 includes a microprocessor (CPU) 24a and a flash memory (FRAM) 24b that is an electrically programmable nonvolatile memory. Various operation control sequences, data required for the sequences, and set values are stored in the FRAM 24b. The CPU 24a reads an operation control sequence and data from the FRAM 24b, develops them. Based on the developed operation control sequence and data, the driving of the diaphragm control circuit 26, light source lamp 27, and filter control circuit 29 is controlled.

On receipt of the luminance signal from the video processor 12, the buffer 25 transfers an electric eye signal (EE signal) to the controller 24.

The diaphragm control circuit 26 controls the driving of the diaphragm motor 31 under the control of the controller 24.

Moreover, for example, red, green, and blue signals used for white balance adjustment are transferred to the CPU 24a, which is included in the controller 24, through the connector 23 of the light source device 13. The red, green, and blue signals may be three synchronized red, green, and blue primary color signals or red, green, and blue field-sequential signals. Moreover, the red, green, and blue signals may be received directly from the video processor 12 or may be transferred from the monitor 14.

The light source lamp 27 comprises a lamp that emits white light, such as, a xenon lamp. The light source lamp 27 is lit with lighting power on which a pulse current is superposed by the pulse lighting circuit 42.

The specific filter 28 comprises a normal filter that passes illumination light emitted from the light source lamp 27 without reducing it at all, a reducing filter that reduces the illumination light to a predetermined light level, and an infrared filter that passes infrared light alone. The filters can be freely placed or removed on or from the path of illumination light, which is emitted from the light source lamp 27, by means of the filter control circuit 29.

The filter control circuit 29 places or removes the specific filter 28 on or from the light path under the control of the controller 24. Moreover, the filter control circuit 29 drives the motor 41 to rotate it, and thus rotates the RGB filter 32 mounted on the rotation shaft of the motor 41.

The RGB filter 32 has three fan-shaped openings formed on the perimeter of a disk-like base thereof. The openings are covered with color transmission filters that passes light rays having wavelengths of red, green, and blue, respectively. The disk-like base is driven to rotate at a predetermined rotating speed by means of the motor 41 under the control of the filter control circuit 29.

When the RGB filter 32 is driven to rotate, each of the red, green, and blue transmission filters is located on the path of illumination light emitted from the light source lamp 27. Consequently, red, green, and blue color light rays, that is, red, green, and blue illumination light rays are successively propagated. The red, green, and blue color light rays propagated from the RGB filter 32 are converged on the condenser lens 33 and introduced to the proximal end of the light guide 15 lying through the endoscope 11.

In FIG. 1, a red transmission filter (32R) that passes light having a wavelength of red is located on the path of illumination light emitted from the light source lamp 27. In this state, red illumination light is supplied to the light guide 15.

The RGB filter 32 has a position index, which indicates the initial point on the RGB filter 32 at which the rotational driving of the RGB filter 32 is started, and a sensor that detects the position index, though the position index and sensor are not shown. The controller 24 receives an output of the sensor, compares the output with a sync signal sent from the video processor 12, and produces a signal which controls the rotational driving of the RGB filter 32. Thus, the RGB filter 32 is controlled via the filter control circuit 29 so that it is driven to rotate synchronously with the sync signal.

In the thus configured endoscope system 1, the object 16 is illuminated with red, green, and blue light rays passed through the RGB filter 32. Namely, the object 16 is sequentially illuminated with field-sequential illumination light.

The object 16 has an optical image thereof converged on the CCD 17 through the objective lens 39. The CCD 17 photoelectrically converts the optical image to produce a field-sequential image signal. The image signal is transferred to the video processor 12.

Figure 2A:
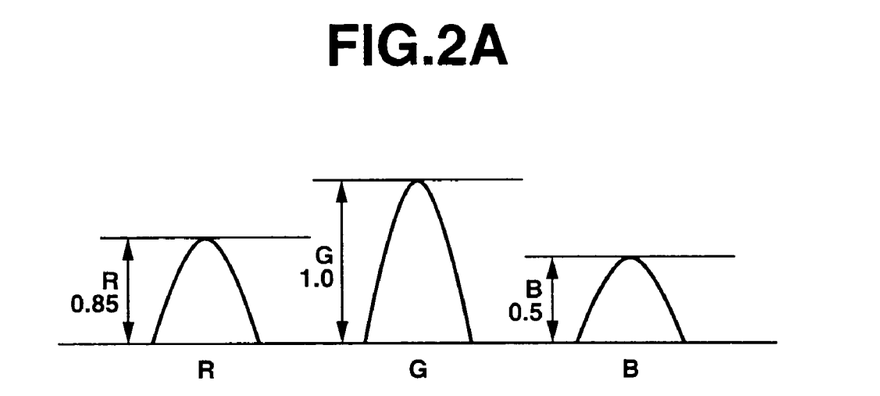
FIG. 2A is an explanatory diagram showing a CCD output signal produced during white balance adjustment in the endoscope system.

When a white object is imaged, the red, green, and blue object video signals received by the video processor 12 have a relationship shown in FIG. 2A. That is to say, assuming that the peak of the green (G) video signal is 1.0, the peak of the red (R) video signal is 0.85 and the peak of the blue (B) video signal is 0.5. When the video signals having the relationship are synthesized, a white balance is obtained.

In other words, when the white object is imaged so that the peak values of red, green, and blue video signals have the above ratio, a television video signal representing white can be produced. The television video signal having a white balance obtained can be transferred to the monitor 14.

The ratio of the red video signal to the green video signal to the blue video signal, that is, R:G:B is 1.52 to 0.5:1.0:0.9 to 0.29.

A worker uses a jig to adjust a trimmer resistor that regulates each of the peak values of the red, green, and blue video signals and that is included in the video processor 12, so that the peak values have a predetermined ratio. In other words, the trimmer resistor is adjusted in order to vary a gain that is given by each of amplifiers associated with the red, green, and blue video signals. Thus, the peak values of the red, green, and blue video signals can be varied or adjusted.

Figure 2B:
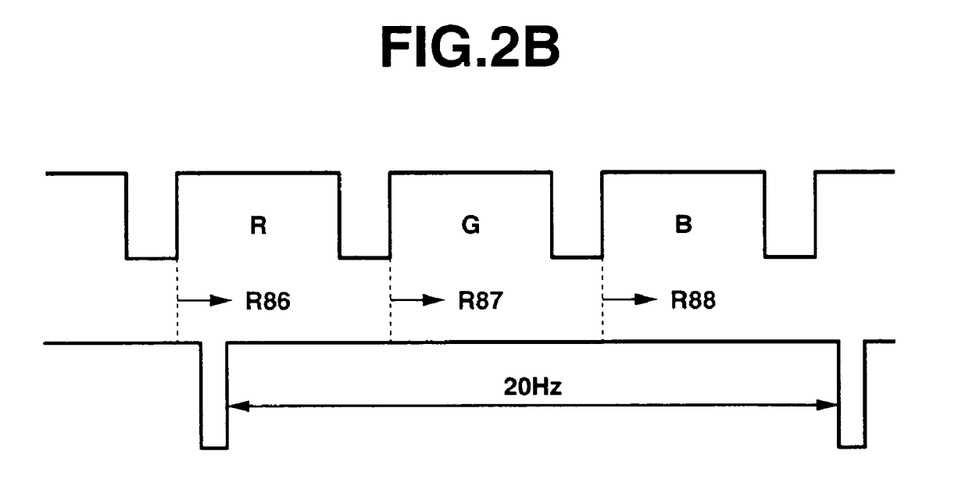
FIG. 2B is an explanatory diagram showing a varying duty cycle of a pulse current that is supplied to a light source lamp which permits generation of red, green, and blue illumination light rays dependent on the setting of a trimmer resistor used to regulate the peak values of signals shown in FIG. 2A.

When the peak values of the red, green, and blue video signals are adjusted, as shown in FIG. 2B, the duty cycle of a pulse current which lights the light source lamp 27 varies depending on the settings of the peak values according to which of the red, green, and blue transmission filters of the RGB filter 32 is located on the light path. Consequently, an amount of illumination light varies.

Assume that the RGB filter 32 makes one rotation at regular intervals, or more particularly, at a frequency of 20 Hz. In this case, when the red (R) transmission filter is located on the light path, a red trimmer resistor R86 varies the duty cycle of a pulse current which is supplied from the pulse lighting circuit 42 and which lights the light source lamp 27.

Consequently, the peak value of the red (R) video signal shown in FIG. 2A is varied. For green (G) or blue (B), a trimmer resistor R87 or R88 for regulating the duty cycle of a pulse current is adjusted so that the ratio of the peak value of the blue video signal to the peak value of the green video signal is set to the aforesaid value.

Specifically, when any of the red, green, and blue transmission filters included in the RGB filer 32 is located on the light path, an irradiation period during which red, green, or light illumination light is irradiated remains constant. However, when the duty cycle of the pulse current which lights the light source lamp 27 is determined for each irradiation period, an amount of illumination light during the irradiation period can be varied. Eventually, white balance adjustment can be achieved.

When the white balance adjustment is achieved as mentioned above, a program describing a white balance automatic adjustment sequence is stored in the FRAM 24b so that a procedure similar to manual adjustment using a trimmer resistor can be performed automatically. According to the white balance automatic adjustment sequence, a white balance is automatically obtained.

The CPU 24a reads the white balance automatic adjustment sequence stored in the FRAM 24b, and develops it. When a white balance adjustment mode is designated, white balance adjustment is automatically executed according to the white balance adjustment sequence.

Figure 3:
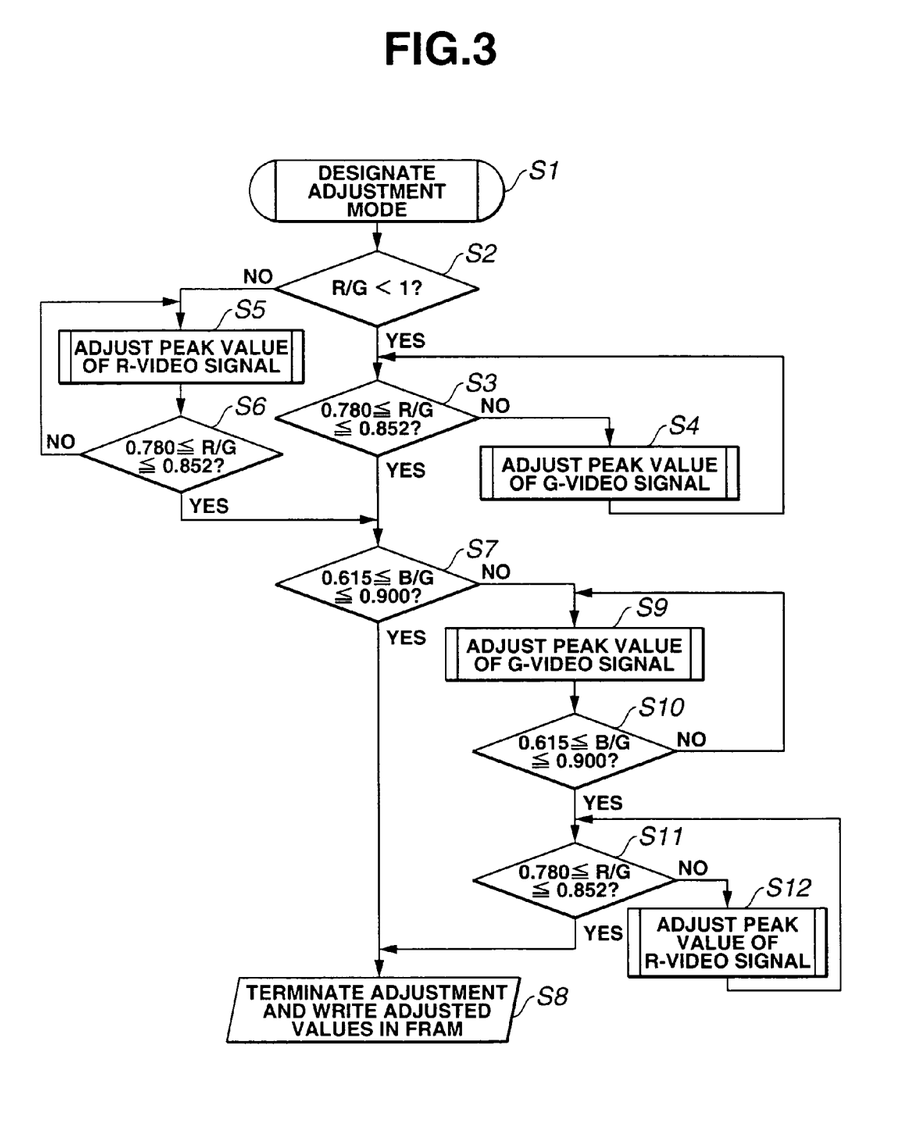
FIG. 3 is a flowchart describing actions for white balance adjustment in the endoscope system.

The white balance adjustment is briefed in conjunction with the flowchart of FIG. 3. The CPU 24a detects the peak values of red, green, and blue video signals produced under red, green, and blue illumination light rays, and compares the peak values thereof one another. As shown in FIG. 1, the CPU 24a includes a comparing function 24c.

The result of the comparison performed by the comparing function 24c included in the CPU 24a is adjusted by varying the amounts of red, green, and blue illumination light rays (the duty cycle of a pulse current according to each irradiation period), so that a condition for a white balance is met.

In other words, the duty cycle of a pulse current is varied according to each irradiation period during which the red, green, or blue illumination light is irradiated. The duty cycle is thus adjusted as shown in FIG. 2B (via the pulse lighting circuit 42) so that the condition under which the video signals whose peak values have the ratio shown in FIG. 2A are produced can be satisfied.

The results of the adjustment are stored as set values (the conditions for light emission under which a white balance is obtained) in a memory means. Thereafter, light is emitted with the duty cycle of a pulse current set to the set values. Resultant red, green, and blue light rays are irradiated.

Specifically, the set values resulting from execution of the white balance automatic adjustment sequence are written in a white balance data storage area 24d in the FRAM 24b. Thereafter, the CPU 24a reads the set values so as to determine the duty cycle of a pulse current supplied from the pulse lighting circuit 42 for each of the irradiation periods for red, green, and blue light rays. Consequently, the red, green, and blue light rays are irradiated with a white balance obtained.

As mentioned above, according to the present embodiment, when the endoscope 11, video processor 12, and light source device 13 are activated, white balance adjustment in the endoscope system 1 is achieved by adjusting the amount of illumination light within the light source device 13.

Compared with a method of obtaining a white balance by adjusting a gain to be given by the video processor 12, the foregoing method has the merit that a signal-to-noise ratio can be optimized. Specifically, according to the method of obtaining a white balance by adjusting a gain by the video processor 12, a case where a gain to a specific color video signal must be larger than gains to the other color video signals often takes place. In contrast, according to the adjusting method of the present embodiment, the gains to the color video signals can be made identical to one another. In this state, the amount of illumination light of a specific color can be increased in order to obtain a white balance. The adjusting method of the present invention can contribute to improvement of a signal-to-noise ratio.

Operations according to the white balance adjustment sequence is described with reference to FIG. 3. When a white balance adjustment button on an operator panel 43 included in the light source device 13 shown in FIG. 1 is pressed, the white balance adjustment sequence is read from the FRAM 24b and developed in the CPU 24a. Consequently, the controller 24 is set to the white balance adjustment mode (step S1).

In order to stabilize an amount of light to be irradiated to the object 16, a lighting current from the pulse lighting circuit 42 to the light source lamp 27 is maximized, and the diaphragm 30 is retained in a certain state.

In this case, as shown in FIG. 1, the white object 16 is, as shown in FIG. 1, opposed to the distal end of the endoscope 11, and illuminated and imaged.

Moreover, the trimmer resistors in the video processor 12 are set to the same resistance, that is, the video processor 12 is set to a state in which the video processor gives the same gain to red, green, and blue video signals.

At step S2, the CPU 24a receives red, green, and blue video signals from the video processor 12 over the communication cable 22, and checks the ratio of the peak value of the red video signal to the peak value of the green video signal. The CPU 24a then determines whether the ratio is smaller than 1.0. When the result of the comparison performed at step S2 demonstrates that the ratio is smaller than 1.0 (R/G<1), step S3 and succeeding steps are performed.

Specifically, depending on the result of the determination made at step S2, it is determined whether the peak value of the red video signal should be regulated (in the light source device 13) or the regulation of the red video signal need not be performed but the peak value of the green video signal should be regulated (in the light source device 13).

When the ratio of the peak value of the red video signal to that of the green video signal (R/G) is determined to be larger than 1 (R/G>1) at step S2, the peak value of the red video signal is regulated at step S5. In order to regulate the peak value of the red video signal, the CPU 24a controls the pulse lighting circuit 42 so that the pulse lighting circuit 42 adjust the duty cycle of a lighting pulse current that is supplied to the light source lamp 27 with the red transmission filter of the RGB filter 32 located on the light path.

At step S5, the duty cycle of the lighting pulse current with the red transmission filter located on the light path is adjusted. Thereafter, at step S46, it is determined whether the ratio of the peak value of the red video signal to that of the green video signal ranges from 0.780 to 0.852 ($0.780 \leq R/G \leq 0.852$).

When it is determined at step S6 that the ratio of the peak value of the red video signal to that of the green video signal ranges from 0.780 to 0.852, step S7 and succeeding steps are performed. When it is determined that the ratio falls outside the range from 0.780 to 0.852, program is returned to step S45. The regulation of the peak value of the red video signal is repeated until the ratio falls within the predetermined range.

When it is determined at step S2 that the ratio of the peak value of the red video signal to that of the green video signal is smaller than 1 (R/G<1), it is determined at step S3 whether the ratio ranges from 0.780 to 0.852 ($0.780 \leq R/G \leq 0.852$). When it is determined at step S3 that the ratio of the peak value of the red video signal to that of the green video signal ranges from 0.780 to 0.852, step S7 and succeeding steps are performed.

When it is determined at step S3 that the ratio of the peak value of the red video signal to that of the green video signal falls outside the range from 0.780 to 0.852 ($0.780 \leq R/G \leq 0.852$), the peak value of the green video signal is regulated at step S4. In order to regulate the peak value of the green video signal, the CPU 24a controls the pulse lighting circuit 42 so that the pulse lighting circuit 42 adjusts the duty cycle of a lighting pulse current that is supplied to the light source lamp 27 with the green transmission filter of the RGB filter 32 located on the light path.

After the duty cycle of the lighting pulse current with the green transmission filter located on the light path is adjusted at step S4, process is returned to step S3. It is determined again whether the ratio of the peak value of the red video signal to that of the green video signal ranges from 0.780 to 0.852 ($0.780 \leq R/G \leq 0.852$). The foregoing procedure is repeated until the ratio ranges from 0.780 to 0.852 ($0.780 \leq R/G \leq 0.852$).

At step S7, it is determined whether the ratio of the peak value of the blue video signal to that of the green video signal (B/G) ranges from 0.615 to 0.900 ($0.615 \leq B/G \leq 0.900$). When it is determined that the ratio ranges from 0.615 to 0.900 ($0.615 \leq B/G \leq 0.900$), at step S8 the adjustment of the duty cycle of the lighting pulse current that is supplied to the light source lamp 27 with each of the red, green, and blue transmission filters of the RGB filter 32 located on the light source is terminated. The resultant duty cycle values are written or stored in the FRAM 24b (which includes the white balance data storage area 24d).

When it is determined at step S7 that the ratio of the peak value of the blue video signal to that of the green video signal falls outside the range from 0.615 to 0.900 ($0.0.615 \leq B/G \leq 0.900$), at step S9 the CPU 24a controls the pulse lighting circuit 42 so that the pulse lighting circuit 42 adjusts the duty cycle of the lighting pulse current that is supplied to the light source lamp 27 with the green transmission filter of the RGB filter 32 located on the light path.

The duty cycle of the lighting pulse current to be supplied with the green transmission filter located on the light path is adjusted at step S9. Thereafter, it is determined at step S10 whether the ratio of the peak value of the blue video signal to that of the green video signal ranges from 0.615 to 0.900. When the ratio is determined to fall outside the range from 0.615 to 0.900, process is returned to step S9. The adjustment is repeated until the ratio ranges from 0.615 to 0.900 ($0.615 \leq B/G \leq 0.900$).

When it is determined at step S10 that the ratio of the peak value of the blue video signal to that of the green video signal ranges from 0.615 to 0.900 (0.615≦B/G≦0.900), it is determined at step S11 whether the ratio of the peak value of the red video signal to that of the green video signal ranges from 0.780 to 0.852. When it is determined that the ratio ranges from 0.780 to 0.85 (0.780≦R/G≦0.85), at step S8 the CPU 24a terminates the adjustment of the duty cycle of the lighting pulse current to the light source lamp 27 with each of the red, green, and blue transmission filters of the RGB filter 32 located on the light path. Moreover, the CPU 24a writes and stores the resultant duty cycle values in the FRAM 24b.

When it is determined at step S11 that the ratio of the peak value of the red video signal to that of the green video signal falls outside the range from 0.780 to 0.85 (0.780≦R/G≦0.852), the duty cycle of the lighting pulse current with the red transmission filter located on the light path is adjusted at step S12. Thereafter, it is determined again at step S11 whether the ratio ranges from 0.780 to 0.852 (0.780≦R/G≦0.852). The adjustment is repeated until the ratio ranges from 0.780 to 0.852 (0.780≦R/G≦50.852).

Incidentally, the range of the values of the ratio of the peak value of the red video signal to that of the green video signal from 0.780 to 0.852 is included in the aforesaid permissible range from 1.52 to 0.5. The range of the values of the ratio of the peak value of the blue video signal to that of the green video signal from 0.615 to 0.900 is included in the aforesaid permissible range from 0.92 to 0.29. These ranges are determined by an operator. The permissible ranges can be determined freely.

As described above, the controller 24 included in the light source device 13 has the white balance adjustment sequence means. Consequently, in the case the light source lamp 27 is replaced with a new one, when the white balance adjustment button on the operator panel 43 is pressed, the duty cycle of the lighting pulse current to the light source lamp 27 can be readily adjusted. Thus, any person other than a skilled person who uses a jig can achieve the white balance adjustment.

By the way, light is emitted from the light source lamp 27, irradiated to the object 16 from the distal end of the insertion member of the endoscope 11 by way of the RGB filter 32 and light guide 15, reflected from the object 16, and converged on the CCD 17. The brightness level of an object image picked up by the CCD must be set to a predetermined brightness level.

Therefore, by driving the diaphragm motor 31, the size of the aperture of the diaphragm 30 (the light limitation level) must be adjusted so that an amount of illumination light required to set the brightness level of a view image to a predetermined brightness level falls on the RGB filter 32.

Figure 4:
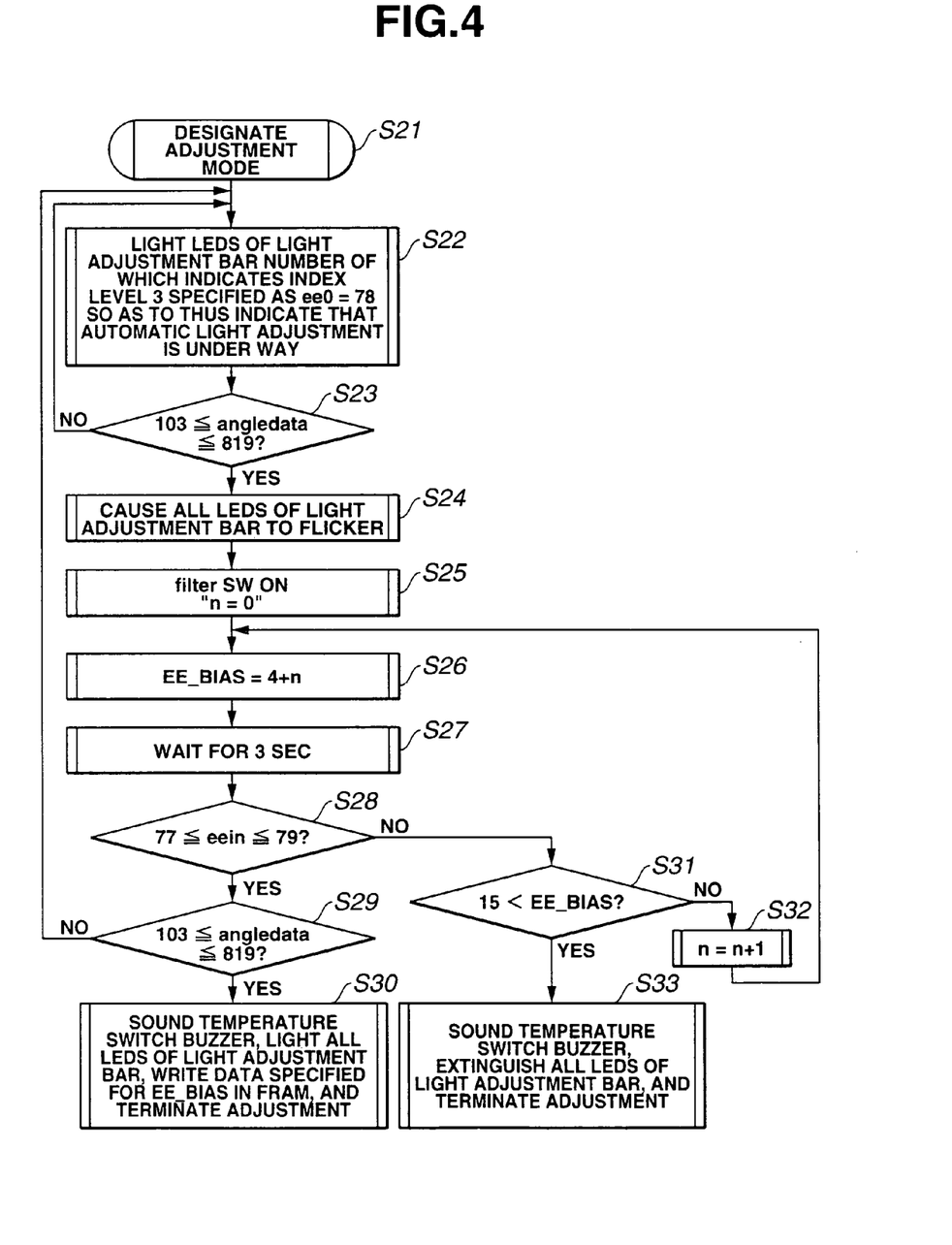
FIG. 4 is a flowchart describing actions for light adjustment in the endoscope system.

The adjustment of an amount of light using the diaphragm 30, that is, light level adjustment is described in conjunction with FIG. 4. When a light level adjustment button on the operator panel 43 is pressed, the CPU 24a reads program data of a light level adjustment sequence from the FRAM 24b in response to the instruction.

The CPU 24a develops the program data of the light level adjustment sequence, and the controller 24 is set to a light level adjustment mode (step S21).

At step S22, the diaphragm 30 is set to a nearly intermediate light limitation level, for example, index level 3. Herein, the index level is a light limitation level associated with each of eight brightness levels from the brightest to the darkest that are adjusted by varying an amount of light.

The diaphragm 30 is set to index level 3 in order to adjust an amount of light at step S22. When the signal level of the luminance signal component of a video signal produced under index level 3 is expressed in the form of digital luminance information of 10 bits long, it is 78 (ee0=78).

In other words, the diaphragm 30 is set to index level 3 by driving the diaphragm motor 31 using the diaphragm control circuit 26.

Furthermore, at step S22, a plurality of LEDs (hereinafter called a light adjustment bar) indicating a light adjusted state and being included in a front panel that is not shown is lit. The light adjustment bar indicating a light adjusted state is composed of, for example, twenty LEDs. The number of lit LEDs indicates a selected index level (in this example, since the diaphragm is set to index level 3, three LEDS are lit). At step S22, LEDs the number of which indicates index level 3 designated as a light adjustment level are lit. Thus, designation of the light adjustment mode is indicated.

At step S23, it is determined whether the angle data angledata of the aperture blades of the diaphragm 30 that is driven to index level 3 at step S22 ranges from 103 to 819 (103≦angledata≦819). An angle-of-aperture blades detection sensor that is not shown and that is included in the diaphragm 30 detects the angle of the aperture blades. An angle detection signal representing the detected angle is converted into data of 10 bits long. The data is presented as the angle data angledata of the aperture blades. When the angle data is 0, the diaphragm 30 is fully closed. When the angle data is 1023, the diaphragm 30 is fully open.

In other words, it is determined whether the angle data of the aperture blades ranges from 103 to 819 (103≦angledata≦819). When the angle data of the aperture blades falls outside the range from 103 to 819 (103≦angledata≦819), the diaphragm 30 is determined to be fully open or fully closed. Process is then returned to step S2. The aforesaid operations are repeated.

When it is determined at step S23 that the angle data of the aperture blades of the diaphragm 30 ranges from 103 to 819 (103≦angledata≦819), the LEDs are caused to flicker at step S24. It is thus notified that light adjustment can be started.

The light adjustment mode is activated through step S22 and step S23, and the diaphragm 30 is set to index level 3, that is, set to an initial state in which adjustment can be started. When the diaphragm 30 cannot be set to the initial state within a predetermined time, for example, although a given time has elapsed, all the LEDs may not flicker at step S24. In this case, it is determined that a light limiting system composed of the diaphragm control circuit 26, diaphragm motor 31, and diaphragm 30 malfunctions. When it is determined that the light limiting system malfunctions, a diaphragm failure indicator LED or a sounding means that is not shown may be driven for notification.

When it is confirmed at step S24 that all the LEDS constituting the light adjustment bar flicker, a filter switch button included in the front panel that is not shown is pressed at step S25. Thus, the filter that does not reduce illumination light is driven to lie on the path of light emanating from the light source lamp 27. Consequently, the CPU 24a actually starts light adjustment. Incidentally, a worker disposes the normal filter on the light path when confirming that the LEDs flicker at step S24.

At step S26, a correction value EE_BIAS used to cause the diaphragm 30 to provide an amount of light associated with index level 3 is set to 4 (EE_BIAS=4+n where n denotes 0). The diaphragm motor 31 is driven using the diaphragm control circuit 26. Incidentally, n denotes a constant.

After the diaphragm motor 31 is driven using the diaphragm control circuit 26 with the correction value EE_BIAS set to 4 (EE_BIAS=4+n where n denotes 0) at step S26, the CPU stands by for approximately 3 sec. at step S27. The 3 sec. at step S27 is a standby time required to stabilize the state of the diaphragm 30 driven by the diaphragm motor 31.

The standby time of 3 sec. elapses at step S27. Thereafter, at step S28, the CCD 17 picks up an image under an amount of light emitted from the diaphragm 30 that is set to index level 3 at step S27. The CPU 24*a* then determines whether luminance information eein specified in a television video signal produced by the video processor 12 is equal to the luminance information (ee0=78) association with index level 3 designated at step S22 (77≦eein≦79).

When the CPU 24*a* determines the received luminance information eein at step S28, the CPU 24*a* may read the luminance information eein received from the video processor 12 a plurality of times, for example, about ten times. The CPU 24*a* may then determine whether an average of read values equals the luminance information eein (77≦eein≦79) associated with index level 3. This would lead to improved precision in determination.

When it is determined at step S28 that the luminance information eein received from the video processor 12 is equal to the luminance information associated with index level 3, the angle data of the aperture blades of the diaphragm 30 is detected at step S29. It is then determined whether the angle data angledata of the aperture blades ranges from 103 to 819 (103≦angledata≦819).

In other words, it is checked whether the diaphragm 30 is not fully open or fully closed. Incidentally, the detection of the angle data of the aperture blades of the diaphragm may be repeated a plurality of times, for example, ten times in order to improve precision in determination. It may then be determined whether an average of detected values equals a predetermined angle data.

When it is determined at step S30 that the angle data angledata of the aperture blades of the diaphragm 30 equals a predetermined value, all the LEDs constituting the light adjustment bar are stopped flickering. The LEDs are all lit or a temperature switch buzzer used to monitor the temperature of the endoscope 11 is driven in order to notify a worker of the termination of light adjustment. Moreover, the correction value EE_BIAS indicating a potential at which the diaphragm 30 is held is written and stored in the FRAM 24*b*.

When it is determined at step S29 that the angle data angledata of the aperture blades of the diaphragm 30 is not equal to the predetermined value, process is returned to step S22. Light adjustment is restarted.

When it is determined at step S28 that the luminance information eein the CPU 24*a* has received from the video processor 12 is not equal to the luminance information associated with index level 3 (77≦eein≦79), it is determined at step S31 whether the correction value indicating a voltage required to hold the diaphragm 30 at index level 3 is an upper limit, for example, 15 or more (15<EE_BIAS). When it is determined that the correction value is the upper limit (15<EE_BIAS), it is determined that the light limiting system malfunctions. At step S33, the flickering LEDs of the light adjustment bar are extinguished or the temperature switch buzzer is driven in order to notify a worker of the malfunction of the light limiting system.

When it is determined at step S31 that the correction value EE_BIAS is equal to or smaller than the upper limit (15>EE_BIAS), the received luminance information eein specified in a video signal produced under the amount of light associated with index level 3 demonstrates that the brightness level specified therein is higher than the one associated with index level 3. Therefore, at step S32, the correction value (EE_BIAS=4+n) designated at step S26 is modified by setting n to n+1. Process is then returned to step S26. At step S26, the correction value is set to 5 (EE_BIAS=4+n=5) in order to narrow the aperture of the diaphragm 30.

In other words, according to the automatic light adjustment of the present invention, the diaphragm 30 is set to a predetermined index level so that luminance information specified in a television video signal produced by the video processor 12 is equal to a predetermined value. A correction value based on which the diaphragm 30 is driven is determined so that the predetermined luminance information can be acquired. This results in high-precision light adjustment.

Moreover, according to the present embodiment, the white balance adjustment button on the operator panel 43 is pressed in order to instruct white balance adjustment. Consequently, the amounts of red, green, and blue field-sequential illumination light rays emanating from the light source device 13 are automatically adjusted in order to obtain a white balance. Even when the endoscope 11 and video processor 12 that are actually employed have different properties, a white balance can be obtained. An environment permitting easy endoscopic examination can be provided.

Moreover, set values resulting from white balance adjustment are written (stored) in the FRAM 24*b* that is an electrically programmable nonvolatile memory. Even if the properties of the light source lamp 27 change due to long-term use or the light source lamp is replaced with a new one, the set values can be readily updated to new ones. Namely, maintenance is easy to do.

Figure 5:
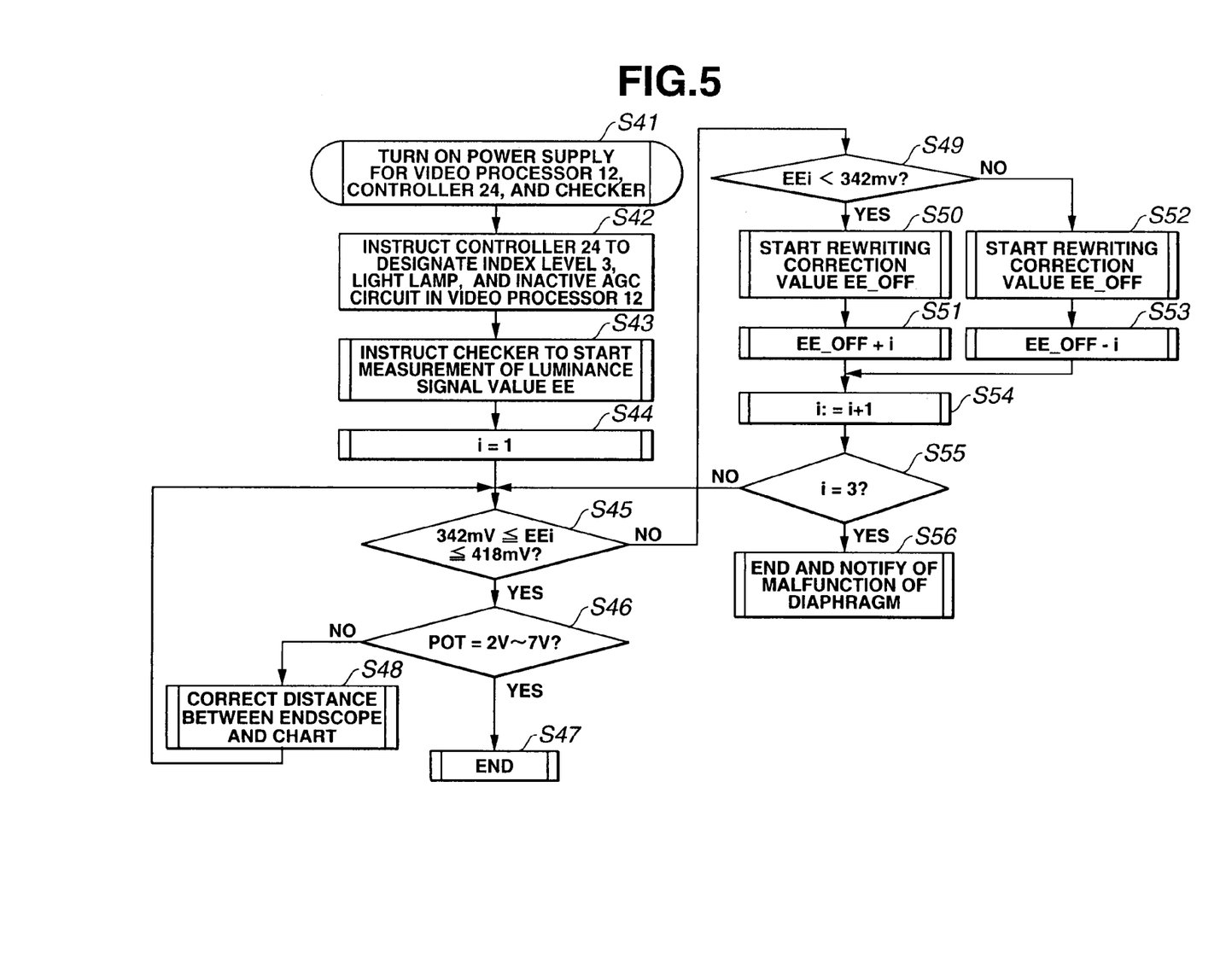
FIG. 5 is a flowchart describing actions for light adjustment in the course of manufacturing an endoscope system in which a second embodiment is implemented.

Next, a second embodiment of automatic light adjustment for the endoscope system 1 is described with reference to FIG. 5. The automatic light adjustment is achieved by adjusting the diaphragm 30 in the course of manufacturing the endoscope system 1. In the course of manufacture, generally, a light adjustment checker is used to adjust an amount of light supplied from the diaphragm 30. The checker is interposed between the video processor 12 and light source device 13, and produces a control signal for light adjustment.

The checker is connected on the communication cable linking the video processor 12 and light source device 13. The driving power supply for the video processor 12, light source device 13, and the checker is then turned on (step S41). When the driving power supply is turned on at step S41, at step S42 the checker transmits a control signal, which indicates index level 3 proportional to the brightness level of an object (an amount of light associated with each of eight brightness levels of an object), to the CPU 24*a* included in the controller 24 of the light source device 13. Moreover, the checker produces a control signal which lights the light source lamp 27 and a control signal which inactivates an automatic gain control circuit (AGC) included in the video processor 12.

At step S43, the checker starts measurement of a luminance signal value EE of a luminance signal sent from the video processor 12 to the controller 24. The luminance signal measured at step S43 is an analog luminance signal.

For the luminance signal value EE measured at step S43, an addition constant i is set to 1 at step S44 (i=1).

At step S45, it is determined whether a luminance signal value EEi resulting from step S44 of adding the addition constant i to the luminance signal value EE measured at step 43 is equal to a predetermined voltage. More particularly, it is determined at step S45 whether the luminance signal value EEi associated with index level 3 is equal to or larger than 342 mv and equal to or smaller than 418 mv (342 mV≦EEi≦418 mV). When the luminance signal value EEi is equal to or smaller than 342 mV, the brightness level of the object is lower than the target brightness level associated with the index level. When the luminance signal value EEi is equal to or larger than 418 mV, the brightness level of the object is higher than the target brightness level associated with the index level.

When it is determined at step S45 that the luminance signal value EEi is equal to or larger than 342 mV and equal to or smaller than 418 mV (342 mV≦EEi≦418 mV), it is determined at step S46 whether an output voltage POT of an angle detection sensor that is not shown and that detects the angle of the aperture blades of the diaphragm 30 ranges from 2 V to 7 V.

When it is determined at step S46 that the output voltage POT of the angle detection sensor proportional to the angle of the aperture blades of the diaphragm 30 falls outside the range from 2 V to 7 V, the position of a light level adjustment chart (not shown) located in front of the distal end of the endoscope 11 is changed at step S48. Step S45 and succeeding steps are then executed again.

When it is determined at step S46 that the output voltage POT of the angle detection sensor proportional to the angle of the aperture blades ranges from 2 V to 7 V, adjustment of the diaphragm 30 is terminated at step S47.

When it is determined at step S45 that the luminance signal value EEi sent from the video processor 12 to the CPU 24a does not meet the condition of 342 mV≦EEi≦418 mV, it is determined at step S49 whether the brightness level of the object indicated by the luminance signal value EEi is lower than the one associated with the index level (EEi<342 mV).

When it is determined at step S49 that the luminance signal value EEi is equal to or smaller than 342 m V (EEi<342 mV), rewriting a correction value EE_OFF based on which the diaphragm is driven is started at step S50. At step S51, a constant i is added to the rewritten diaphragm driving correction value EE_OFF. Consequently, the resultant diaphragm driving correction value EE_OFF+i is designated.

At step S51, the constant i is added to the rewritten diaphragm driving correction value EE_OFF. At step S54, the constant i is incremented by 1 (i=i+1). At step S55, it is determined whether the constant i equals 3 (i=3). When the constant i is not equal to 3, the diaphragm 30 is driven based on the added diaphragm driving correction value EE_OFF+i. Step S45 and succeeding steps are then carried out. When it is determined at step S55 that the constant i equals 3 (i=3), it is determined that the diaphragm 30 malfunctions. At step S56, light adjustment is terminated and the malfunction of the diaphragm 30 is notified.

In other words, when the brightness level of the object is lower than the one associated with index level 3 designated during the light adjustment, the diaphragm is driven with the constant i varied in three steps. Even when the constant i becomes equal to 3, when the diaphragm does not enter a predetermined state, the diaphragm 30 is determined to malfunction.

When it is determined at step S49 that the luminance signal value EEi is not equal to or smaller than 342 mV, the luminance signal value EEi may be larger than 418 mV, that is, the brightness level of the object may be higher than the one associated with index level 3. In this case, at step S52, the luminance signal value EEi is rewritten into the luminance signal value EE_OFF associated with the fully open state. At step S53, the constant i is subtracted from the rewritten luminance signal value EE_OFF in order to designate a subtracted luminance signal value EE_OFF−i.

At step S53, the constant i is subtracted from the rewritten luminance signal value EE_OFF. At step S54, the constant i is incremented by one (i=i+1). At step S55, it is determined whether the constant i equals 3. When it is determined that the constant i is not equal to 3, the diaphragm 30 is driven based on the subtracted diaphragm driving correction value EE_OFF−i. Step S45 and succeeding steps are carried out. When it is determined at step S55 that the constant i equals 3 (i=3), it is determined that the diaphragm 30 malfunctions. At step S56, light adjustment is terminated and the malfunction of the diaphragm is notified.

In other words, when the brightness level of the object is higher than the one associated with index level 3, the diaphragm is first driven to the fully open state and then further driven with the constant i varied in three steps. Although the constant i equals 3, when the diaphragm does not enter a predetermined state, the diaphragm is determined to malfunction.

As described above, since the checker is employed, the diaphragm 30 can be adjusted to have an aperture size permitting an appropriate amount of light. Moreover, the fact that the diaphragm 30 cannot be driven can be immediately discovered.

INDUSTRIAL APPLICABILITY

As described so far, when an adjusting method for endoscope systems in accordance with the present invention is implemented in an endoscope system, there is provided a user-friendly endoscope system in which white balance adjustment and light level adjustment can be performed immediately. Moreover, it is unnecessary to use an adjustment jig at the time of replacing a light source lamp with a new one or at the time of maintenance inspection, and it is also unnecessary to get skilled in adjustment work.

The invention claimed is:

1. An adjusting method for an endoscope system, comprising:
    a detection step of detecting, in order to adjust white balance of illumination light rays, an image signal for each of first, second and third ranges of wavelengths reflected from a subject, correspondingly to irradiations of first, second and third illumination light rays, respectively;
    a first step of comparing a ratio of peak values of first and second image signals with a reference value;
    a second step of adjusting light amounts of the first and second illumination light rays, correspondingly to a result of the first step;
    a third step of determining whether or not a ratio of peak values of the second and third image signals is within a first setting range, correspondingly to a result of the second step; and
    a fourth step of readjusting the light amounts of the first and second illumination light rays, correspondingly to a result of the third step.

2. The method according to claim 1, wherein the second step comprises:

when a determination result of the first step is smaller than the reference value, adjusting the light amount of the second illumination light ray so that the ratio of the peak values of the first and second image signals is within a second setting range; and when a determination result of the first step is larger than the reference value, adjusting the light amount of the first illumination light ray so that the ratio of the peak values of the first and second image signals is within a second setting range.

3. The method according to claim 1, wherein the fourth step comprises:

when a determination result of the third step is out of the first setting range, adjusting the light amount of the second illumination light my so that the ratio of the peak values of the second and third image signals is within the first setting range.

4. The method according to claim 3, wherein the fourth step further comprises:

when a peak value of the second illumination light is readjusted, determining whether or not a ratio of peak values of the first image signal and the second image signal after the readjustment is within the second setting range; and when the ratio is out of the second setting range, adjusting the light amount of the first illumination light ray so that the ratio of the peak values of the first and second image signals is within the second setting range.

5. The method according to claim 3, further comprising:

an automatic adjustment starting step of reading a sequence for performing an automatic adjustment operation for automatically performing the first to fourth steps, after the detection step; and an automatic adjustment ending step of recording an adjustment result and ending the automatic adjustment operation, after the fourth step.

6. The method according to claim 1, wherein in the second and fourth steps, the light amounts of the first and sceond illumination light rays are adjusted by adjusting a duty of a pulse current outputted to a light source lamp.

7. The method according to claim 1, further comprising after the fourth step:

a diaphragm adjusting step of adjusting a diaphragm that controls an amount of light irradiated from a light source lamp.

8. The method according to claim 1, wherein the first, second and third image signals are RGB signals that correspond to red, green and blue signals, respectively.

9. An endoscope system, comprising:

a light source lamp of emitting illumination light rays;

an optical filter of switching the illumination light rays emitted by the light source lamp into field sequential iliumination lights having first, second and third wavelengths, respectively;

an image capturing device of capturing an image of a subject illuminated by the field sequential illumination lights and outputting first, second and third color signals corresponding to a captured image;

a control portion of controlling operations of an adjustment portion based on the first, second and third color signals, thereby performing an operation of adjusting white balance of the field sequential illumination lights, the adjustment portion including:

a detection portion of detecting, in order to adjust white balance of illumination light rays, an image signal for each of first, second and third ranges of wavelengths reflected from a subject, correspondingly irradiations of first, second and third illumination light rays, respectively;

a comparison portion of comparing a ratio of peak values of first and second image signals with a reference value;

a light amount adjustment portion of adjusting light amounts of the first and second illumination light rays, correspondingly to a result of comparison by the comparison portion;

a determination portion of determining whether or not a ratio of peak values of the second and a third image signals is within a first setting range, correspondingly to a result of adjustment by thc light amount adjustment portion; and a light amount readjustment portion of readjusting the light amounts of the first and second illumination light rays, correspondingly to a result of determination by the determination portion;

an adjustment instructing portion of making the control portion execute the white balance adjusting operation; and a recording portion of recording a result of the white balance adjustment by the control portion.

* * * * *